(12) United States Patent
Ammermann et al.

(10) Patent No.: US 6,979,666 B2
(45) Date of Patent: Dec. 27, 2005

(54) DITHIANON-BASED FUNGICIDAL MIXTURES

(75) Inventors: Eberhard Ammermann, Heppenheim (DE); Reinhard Stierl, Freinsheim (DE); Ulrich Schöfl, Brühl (DE); Klaus Schelberger, Gönnheim (DE); Maria Scherer, Godramstein (DE); Michael Henningsen, Frankenthal (DE); Randall Even Gold, Obrigheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/517,703

(22) PCT Filed: Jun. 30, 2003

(86) PCT No.: PCT/EP03/06887

§ 371 (c)(1),
(2), (4) Date: Dec. 13, 2004

(87) PCT Pub. No.: WO2004/004461

PCT Pub. Date: Jan. 15, 2004

(65) Prior Publication Data

US 2005/0209258 A1   Sep. 22, 2005

(30) Foreign Application Priority Data

Jul. 8, 2002  (DE) .................... 102 30 802

(51) Int. Cl.[7] ............... A01N 43/60; A01N 43/54; A61K 31/505
(52) U.S. Cl. ..................... 504/136; 514/275
(58) Field of Search .............. 514/275; 504/136

(56) References Cited

U.S. PATENT DOCUMENTS 5,532,262 A   7/1996   Brandes et al.

FOREIGN PATENT DOCUMENTS

EP   0 236 689 A2   9/1987
GB   857383   10/1958

*Primary Examiner*—Alton Pryor
(74) *Attorney, Agent, or Firm*—Birch, Stewart, Kolasch & Birch, LLP

(57) ABSTRACT

Fungicidal mixtures, comprising
A) the compound of the formula I

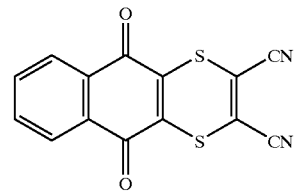

and
B) a pyrimidine derivative of the formula II,

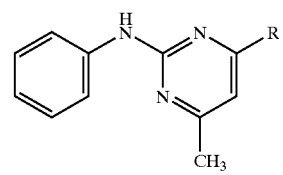

in which R is methyl, cyclopropyl or 1-propynyl, in a synergistically effective amount, methods for controlling harmful fungi using mixtures of compounds I and II and the use of the compounds I and II for preparing such mixtures are described.

8 Claims, No Drawings

DITHIANON-BASED FUNGICIDAL MIXTURES

The present invention relates to fungicidal mixtures, comprising
A) the compound of the formula I

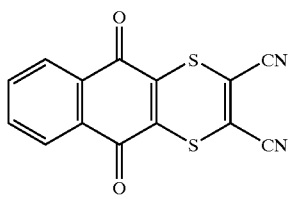

and
B) a pyrimidine derivative of the formula II,

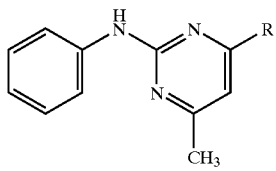

in which R is methyl, cyclopropyl or 1-propynyl in a synergistically effective amount.

Moreover, the invention relates to methods for controlling harmful fungi using mixtures of the compounds I and II and to the use of the compounds I and II for preparing such mixtures.

The compound of the formula I (common name: dithianon) and processes for its preparation are described in GB-A 857 383.

The compounds of the formula II, their preparation and their action against harmful fungi are likewise known from the literature:

| Compound No. | R | common name | Literature |
|---|---|---|---|
| II-1 | methyl | pyrimethanil | DD-A 151 404 |
| II-2 | cyclopropyl | cyprodinil | EP-A 310 550 |
| II-3 | 1-propynyl | mepanipyrim | EP-A 224 339 |

It is an object of the present invention to provide mixtures which have improved activity against harmful fungi combined with a reduced total amount of active compounds applied (synergistic mixtures), with a view to reducing the application rates of broadening the activity spectrum of the known compounds. We have found that this object is achieved by the mixtures defined at the outset. Moreover, we have found that applying the compounds I and II simultaneously, i.e. together or separately, or applying the compounds I and II in succession provides better control of harmful fungi than is possible with the individual compounds alone.

Usually, what are applied are mixtures of the compound I with one pyrimidine derivative II. However, in certain cases mixtures of the compound I with two or more pyrimidine derivatives II may be advantageous.

Particular preference is given to the compounds II-1 and II-2.

Owing to their basic character, the compounds II-1 to II-3 are capable of forming salts or adducts with inorganic or organic acids or with metal ions.

Examples of inorganic acids are hydrohalic acids, such as hydrogen fluoride, hydrogen chloride, hydrogen bromide and hydrogen iodide, sulfuric acid, phosphoric acid, carbonic acid and nitric acid.

Suitable organic acids are, for example, formic acid, and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals with 1 to 20 carbon atoms), arylsulfonic acids or aryldisulfonic acids (aromatic radicals, such as phenyl and naphthyl, which carry one or two sulfo groups), alkylphosphonic acids (phosphonic acids having straight-chain or branched alkyl radicals with 1 to 20 carbon atoms), arylphosphonic acids or aryldiphosphonic acids (aromatic radicals, such as phenyl and naphthyl, which carry one or two phosphonic acid radicals), it being possible for the alkyl or aryl radicals to carry further substituents, for example p-toluenesulfonic acid, salicylic acid, p-aminosalicylic acid, 2-phenoxybenzoic acid, 2-acetoxybenzoic acid, etc.

Suitable metal ions are, in particular, the ions of the elements of the second main group, in particular calcium and magnesium, of the third and fourth main group, in particular aluminum, tin and lead, and of the first to eighth transition group, in particular chromium, manganese, iron, cobalt, nickel, copper, zinc, and others. Particular preference is given to the metal ions of the elements of the transition groups of the fourth period. The metals can be present in the various valences which they can assume.

When preparing the mixtures, it is preferred to employ the pure active compounds I and II, with which further active compounds against harmful fungi or other pests, such as insects, arachnids or nematodes, or else herbicidal or growth-regulating active compounds or fertilizers can be admixed as required.

The mixtures of the compounds I and II, or the simultaneous joint or separate use of the compounds I and II, have outstanding action against a wide range of phytopathogenic fungi, in particular from the classes of the *Ascomycetes, Deuteromycetes, Oomycetes* and *Basidiomycetes*. Some of them act systemically and are therefore also suitable for use as foliar- and soil-acting fungicides.

They are especially important for controlling a large number of fungi in a variety of crop plants, such as cotton, vegetable species (for example cucumbers, beans and cucurbits), barley, grass, oats, coffee, corn, fruit species, rice, rye, soya, grapevine, wheat, ornamentals, sugarcane, and a variety of seeds.

They are particularly suitable for controlling the following phytopathogenic fungi: *Erysiphe cichoracearum* and *Sphaerotheca fuliginea* in cucurbits, *Podosphaera leucotricha* in apples, *Uncinula necator* in grapevines, *Rhizoctonia* species in cotton, rice and lawns, *Ustilago* species in cereals and sugarcane, *Venturia inaequalis* (scab) in apples, *Septoria nodorum* in wheat, *Botrytis cinerea* (gray mold) in strawberries, vegetables, ornamentals and grapevines, *Cercospora arachidicola* in groundnuts, *Pseudocercosporella herpotrichoides* in wheat and barley, *Phytophthora infestans* in potatoes and tomatoes, *Pseudoperonospora* species in cucurbits and hops, *Plasmopara viticola* in grapevines, *Alternaria* species in vegetables and fruit and *Fusarium* and *Verticillium* species.

The compounds I and II can be applied simultaneously, that is either together or separately, or in succession, the sequence, in the case of separate application, generally not having any effect on the control measures.

The compounds I and II are usually applied in a weight ratio of from 10:1 to 1:100, preferably from 1:1 to 1:10, in particular from 1:1 to 1:5.

Correspondingly, the application rates of the compound I are generally from 5 to 2000 g/ha, preferably from 10 to 1000 g/ha, in particular from 50 to 750 g/ha.

Depending on the nature of the desired effect, the application rates of the mixtures according to the invention are, for the compounds II, from 5 g/ha to 500 g/ha, preferably from 50 to 500 g/ha, in particular from 50 to 200 g/ha.

For seed treatment, the application rates of the mixture are generally from 0.001 to 1 g/kg of seed, preferably from 0.01 to 0.5 g/kg, in particular from 0.01 to 0.1 g/kg.

If phytopathogenic harmful fungi are to be controlled, the separate or joint application of the compounds I and II or of the mixtures of the compounds I and II is effected by spraying or dusting the seeds, the plants or the soils before or after sowing, or before or after plant emergence.

The fungicidal synergistic mixtures according to the invention, or the compounds I and II, can be formulated, for example, in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in each case, it should ensure as fine and uniform a distribution as possible of the mixture according to the invention.

The formulations are prepared in a manner known per se, for example by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, for example ligno-, phenol-, naphthalene- and dibutylnaphthalenesulfonic acids, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenyl ether, ethoxylated isooctyl-, octyl- or nonylphenol, alkylphenyl polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methyl cellulose.

Powders, materials for broadcasting and dusts can be prepared by mixing or jointly grinding the compounds I and II or the mixture of the compounds I and II with a solid carrier.

Granules (for example coated granules, impregnated granules or homogeneous granules) are usually prepared by binding the active compound, or active compounds, to a solid carrier.

Fillers or solid carriers are, for example, mineral earths, such as silica gel, silicic acids, silicates, talc, kaolin, limestone, lime, chalk, bole, loess, clay, dolomite, diatomaceous earth, calcium sulfate, magnesium sulfate, magnesium oxide, ground synthetic materials, and fertilizers, such as ammonium sulfate, ammonium phosphate, ammonium nitrate, ureas and products of vegetable origin, such as cereal meal, tree bark meal, wood meal and nutshell meal, cellulose powders or other solid carriers.

The formulations generally comprise from 0.1 to 95% by weight, preferably from 0.5 to 90% by weight, of one of the compounds I and II or of the mixture of the compounds I and II. The active compounds are employed in a purity of from 90% to 100%, preferably from 95% to 100% (according to NMR spectrum or HPLC).

The compounds I and II, the mixtures or the corresponding formulations are applied by treating the harmful fungi, or the plants, seeds, soils, areas, materials or spaces to be kept free from them with a fungicidally effective amount of the mixture, or of the compounds I and II in the case of separate application. Application can be effected before or after infection by the harmful fungi.

Examples of such preparations comprising the active compounds are:

I. a solution of 90 parts by weight of the active compounds and 10 parts by weight of N-methylpyrrolidone; this solution is suitable for use in the form of microdrops;

II. a mixture of 20 parts by weight of the active compounds, 80 parts by weight of xylene, 10 parts by weight of the adduct of 8 to 10 mol of ethylene oxide to 1 mol of oleic acid N-monoethanolamide, 5 parts by weight of the calcium salt of dodecylbenzenesulfonate, 5 parts by weight of the adduct of 40 mol of ethylene oxide and 1 mol of castor oil; a dispersion is obtained by finely distributing the solution in water;

III. an aqueous dispersion of 20 parts by weight of the active compounds, 40 parts by weight of cyclohexanone, 30 parts by weight of isobutanol, 20 parts by weight of the adduct of 40 mol of ethylene oxide and 1 mol of castor oil;

IV. an aqueous dispersion of 20 parts by weight of the active compounds, 25 parts by weight of cyclohexanol, 65 parts by weight of a mineral oil fraction of boiling point 210 to 280° C., and 10 parts by weight of the adduct of 40 mol of ethylene oxide and 1 mol of castor oil;

V. a mixture, ground in a hammer mill, of 80 parts by weight of the active compounds, 3 parts by weight of the sodium salt of diisobutylnaphthalene-1-sulfonate, 10 parts by weight of the sodium salt of a lignosulfonic acid from a sulfite waste liquor and 7 parts by weight of pulverulent silica gel; a spray mixture is obtained by finely distributing the mixture in water;

VI. an intimate mixture of 3 parts by weight of the active compounds and 97 parts by weight of finely divided kaolin; this dust comprises 3% by weight of active compound;

VII. an intimate mixture of 30 parts by weight of the active compounds, 92 parts by weight of pulverulent silica gel and 8 parts by weight of paraffin oil which had been sprayed onto the surface of this silica gel; this formulation imparts good adhesion to the active compound;

VIII. a stable aqueous dispersion of 40 parts by weight of the active compounds, 10 parts by weight of the sodium salt of a phenolsulfonic acid/urea/formaldehyde condensate, 2 parts by weight of silica gel and 48 parts by weight of water; this dispersion may be diluted further;

IX. a stable oily dispersion of 20 parts by weight of the active compounds, 2 parts by weight of the calcium salt of dodecylbenzenesulfonate, 8 parts by weight of fatty alcohol polyglycol ether, 20 parts by weight of the sodium salt of a phenolsulfonic acid/urea/formaldehyde condensate and 88 parts by weight of a paraffinic mineral oil.

The fungicidal activity of the compound and of the mixtures can be demonstrated by the following experiments:

The active compounds, separately or together, were prepared as a stock solution with 0.25% by weight of active compound in acetone or DMSO. 1% by weight of the emulsifier Uniperol® EL (wetting agent having emulsifying and dispersing action based on ethoxylated alkylphenols) was added to this solution, and the solution was diluted with water to the desired concentration.

Use example: Activity against early blight of tomato caused by *Alternaria solani*

Leaves of potted plants of the cultivar "Große Fleischtomate St. Pierre" were sprayed to runoff point with an aqueous suspension having the concentration of active compound stated below. The next day, the leaves were infected with an aqueous spore suspension of *Alternaria solani* in a 2% strength biomalt solution having a density of $0.17 \times 10^6$ spores/ml. The plants were then placed in a water-vapor-saturated chamber at 20–22° C. After 5 days, the early blight on the untreated, but infected control plants had developed to such an extent that the infection could be determined visually in %.

Evaluation is carried out by determining the infected leaf areas in percent. These percentages are converted into efficacies.

The efficacy (E) is calculated as follows using Abbot's formula:

$$E = (1 - \alpha/\beta) \cdot 100$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the active compound mixtures are determined using Colby's formula [S.R. Colby, Weeds 15, 20–22 (1967)] and compared with the observed efficacies.

Colby's Formula:

$$E = x + y - x \cdot y / 100$$

E expected efficacy, expressed in percent of the untreated control, when using the mixture of the active compounds A and B at the concentrations a and b x efficacy, expressed in % of the untreated control, when using active compound A at a concentration of a y efficacy, expressed in % of the untreated control, when using active compound B at a concentration of b

TABLE A individual active compounds

| Example | Active compound | Concentration of active compound in the spray liquid [ppm] | Efficacy in % of the untreated control |
|---|---|---|---|
| 1 | Control (untreated) | (72% infection) | 0 |
| 2 | I (dithianon) | 63 | 86 |
|   |   | 31 | 79 |
|   |   | 16 | 65 |
|   |   | 8 | 44 |
| 3 | II-1 (pyrimethanil) | 63 | 0 |
|   |   | 31 | 0 |
|   |   | 16 | 0 |
|   |   | 8 | 0 |
| 4 | II-2 (cyprodinil) | 63 | 86 |
|   |   | 16 | 72 |
|   |   | 8 | 44 |

TABLE B combinations according to the invention

| Example | Mixture of active compounds Concentration Mixing ratio | Observed efficacy | Calculated efficacy*) |
|---|---|---|---|
| 6 | I + II-1 63 + 8 ppm 8:1 | 99 | 85 |
| 7 | I + IIa 15 + 1.5 ppm 10:1 | 94 | 67 |
| 8 | I + IIa 3.75 + 3 ppm 1.25:1 | 99 | 78 |
| 9 | I + IIa 3.75 + 6 ppm 1:1.6 | 100 | 89 |
| 10 | I + IIb-1 7.5 + 0.75 ppm 10:1 | 44 | 0 |
| 11 | I + IIb-1 3.75 + 0.375 ppm 10:1 | 56 | 0 |
| 12 | I + IIb-1 3.75 + 3 ppm 1.25:1 | 61 | 44 |

*)efficacy calculated using Colby's formula

The test results show that for all mixing ratios the observed efficacy of the mixtures according to the invention is considerably higher than that predicted using Colby's formula.

We claim:

1. A fungicidal mixture, comprising
A) the compound of the formula I

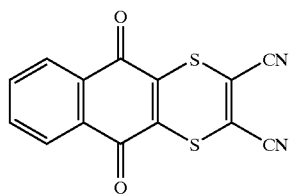

I and

B) a pyrimidine derivative of the formula II,

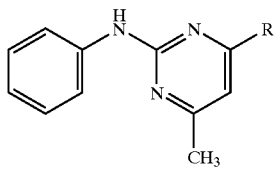

in which R is methyl, cyclopropyl or 1-propynyl, in a synergistically effective amount.

2. The fungicidal mixture as claimed in claim 1, comprising, as the pyrimidine derivative II, the compound II-1.

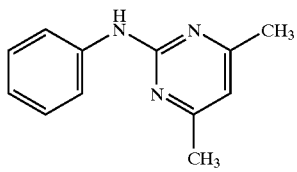

3. The fungicidal mixture as claimed in claim 1 or 2, wherein the weight ratio of the compound I to the compound II is from 10:1 to 1:100.

4. The fungicidal composition, comprising a solid or liquid carrier and the mixture as claimed in claim 1.

5. A method for controlling harmful fungi, which comprises treating the harmful fungi, their habitat, or plants, seeds, soils, areas, materials or spaces to be kept free from them with the compound of the formula I and a compound of the formula II as set forth in claim 1.

6. A method as claimed in claim 5, which comprises treating the harmful fungi, their habitat, or the plants, seeds, soils, areas, materials or spaces to be kept free from them with from 5 to 2000 g/ha of the compound I as set forth in claim 1.

7. A method as claimed in claim 5, which comprises treating the harmful fungi, their habitat, or the plants, seeds, soils, areas, materials or spaces to be kept free from them with from 5 to 500 g/ha of at least one compound II as set forth in claim 1.

8. A method of preparing the mixture as claimed in claim 1, which comprises mixing together the compounds of the formulae I and II as set forth in claim 1.

* * * * *